United States Patent
Bekemeier et al.

(10) Patent No.: US 9,017,650 B2
(45) Date of Patent: Apr. 28, 2015

(54) EMULSIONS OF AMINOFUNCTIONAL SILICONES

(75) Inventors: Thomas Daniel Bekemeier, Birch Run, MI (US); Anne-Lise Girboux, Jurbise (BE); Marie-Agnes Leboucher, Lasne (BE); Scott B. Poplawski, Freeland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 13/811,303

(22) PCT Filed: Jul. 20, 2011

(86) PCT No.: PCT/US2011/044670
§ 371 (c)(1),
(2), (4) Date: Jan. 21, 2013

(87) PCT Pub. No.: WO2012/012524
PCT Pub. Date: Jan. 26, 2012

(65) Prior Publication Data
US 2013/0121949 A1 May 16, 2013

Related U.S. Application Data

(60) Provisional application No. 61/366,313, filed on Jul. 21, 2010.

(51) Int. Cl.
| | | |
|---|---|---|
| A61Q 5/12 | (2006.01) |
| A61Q 5/02 | (2006.01) |
| A61K 31/695 | (2006.01) |
| A61K 8/06 | (2006.01) |
| A61K 8/41 | (2006.01) |
| A61K 8/86 | (2006.01) |
| A61K 8/891 | (2006.01) |
| A61K 8/898 | (2006.01) |
| A61Q 19/00 | (2006.01) |
| C08J 3/05 | (2006.01) |
| C08L 83/04 | (2006.01) |
| B01F 17/00 | (2006.01) |
| B01F 17/54 | (2006.01) |
| C08G 77/26 | (2006.01) |

(52) U.S. Cl.
CPC ............. *A61K 8/062* (2013.01); *A61K 8/416* (2013.01); *A61K 8/86* (2013.01); *A61K 8/891* (2013.01); *A61K 8/898* (2013.01); *A61K 2800/10* (2013.01); *A61Q 19/00* (2013.01); *C08G 77/26* (2013.01); *C08J 3/05* (2013.01); *C08J 2383/04* (2013.01); *C08J 2383/08* (2013.01); *C08J 2483/08* (2013.01); *C08L 83/04* (2013.01); *A61Q 5/12* (2013.01); *B01F 17/005* (2013.01); *B01F 17/0071* (2013.01); *Y10S 514/937* (2013.01)

(58) Field of Classification Search
CPC ............. C08J 2383/04; C08J 3/03; C08J 3/05; C08J 2383/08; C08J 2483/08; A61Q 19/00; A61Q 5/02; A61Q 5/12; A61K 8/062; A61K 2800/21; A61K 8/892; A61K 8/895; A61K 8/416; A61K 8/891; A61K 8/898; A61K 2800/10; A61K 8/86; C08L 83/08; C08L 83/04; B01F 17/0071; B01F 17/005; C08G 77/26
USPC ............... 524/588, 837; 516/53, 55, 924; 106/287.11; 428/391; 442/102; 514/63, 514/788, 937; 525/477; 424/70.122
See application file for complete search history.

(56) References Cited

U.S. PATENT DOCUMENTS

| | | | | |
|---|---|---|---|---|
| 2006/0111452 | A1* | 5/2006 | Wallace et al. | 516/53 |
| 2007/0043123 | A1* | 2/2007 | Creutz et al. | 516/55 |

FOREIGN PATENT DOCUMENTS

| | | |
|---|---|---|
| WO | 2007136708 | 11/2007 |
| WO | 2008142658 | 11/2008 |

* cited by examiner

*Primary Examiner* — Blessing M Fubara
(74) *Attorney, Agent, or Firm* — Baltazar Gomez; Alan Zombeck

(57) ABSTRACT

Aminofunctional silicone emulsions are prepared by forming a mixture of A) 100 parts of a polydialkylsiloxane Having a viscosity of at least 50,000 mm/s at 23° C., and B) 0.1 to 100 parts of an aminofunctional organopolysiloxane, admixing C) 0.1 to 50 parts of a halide free quaternary ammonium surfactant containing at least 10 carbon atoms, and a sufficient amount of water to form an emulsion.

12 Claims, No Drawings

EMULSIONS OF AMINOFUNCTIONAL SILICONES

CROSS REFERENCE TO RELATED APPLICATIONS

This application is a U.S. national stage filing under 35 U.S.C. §371 of PCT Application No. PCT/US11/44670 filed on Jul. 20, 2011, currently pending, which claims the benefit of U.S. Provisional Patent Application No. 61/366,313 filed Jul. 21, 2010 under 35 U.S.C. §119 (e). PCT Application No. PCT/US11/44670 and U.S. Provisional Patent Application No. 61/366,313 are hereby incorporated by reference.

BACKGROUND OF THE INVENTION

Emulsions of aminofunctional silicones and high molecular weight silicones are widely used in hair care compositions to provide various aesthetic benefits. Various types of emulsions have been commercially developed to provide water based products of such aminofunctional silicone polymers for use as hair conditioning agents. One method to prepare aminofunctional silicone emulsions involves emulsion polymerization techniques, where siloxane monomers are first emulsified, and then subsequently polymerized to a high molecular weight. Alternatively, mechanical emulsions may be prepared from pre-formed aminofunctional silicones.

Reducing the presence of solvents, un-reacted siloxanes, catalyst residues, cyclic polymerization byproducts, and other impurities in silicone emulsions is an ongoing challenge in the art. The need to reduce such impurities may arise, among other reasons, when such impurities are incompatible with downstream applications (for example, medical, cosmetic, and personal care applications), where the presence of such impurities would reduce the stability of an emulsion, or where regulatory requirements require removal or reduction of their presence. In particular, there is an interest to reduce the presence of cyclosiloxanes, such as octamethylcyclotetrasiloxanes and decamethylcyclopentasiloxanes, in silicone emulsions.

The present inventors have discovered a process for producing mechanical emulsions of aminofunctional siloxanes having reduced content of cyclosiloxanes. Thus, the amount of octamethylcyclotetrasiloxanes and decamethylcyclopentasiloxanes in the emulsions produced by the present inventive process is reduced when compared to emulsions prepared by conventional methods. The resulting emulsions are particularly useful in hair care products.

BRIEF SUMMARY OF THE INVENTION

The present invention relates to a process for preparing an aminofunctional silicone emulsion comprising:
I) forming a mixture of;
A) 100 parts of a polydialkylsiloxane having a viscosity of at least 50,000 mm$^2$/s at 23° C.,
B) 0.1 to 100 parts of an aminofunctional organopolysiloxane,
II) admixing;
C) 0.1 to 50 parts of a halide free quaternary ammonium surfactant containing at least 10 carbon atoms,
and a sufficient amount of water to form an emulsion,
III) optionally, further shear mixing the emulsion.

The present invention also relates to the emulsions produced by the present methods. The inventive process provides aminofunctional silicone emulsions having a volatile siloxane content that is less than 1 weigh percent of the total silicone content of the emulsion.

DETAILED DESCRIPTION OF THE INVENTION

The first step in the present process involves
I) forming a mixture of;
A) 100 parts of a polydialkylsiloxane having a viscosity of at least 50,000 mm$^2$/s at 23° C., and
B) 0.1 to 100 parts of an aminofunctional organopolysiloxane.

A) The Polydialkylsiloxane

Component A) in the present process is a polydialkylsiloxane. Component A) may be selected from polydialkylsiloxanes having the general formula;

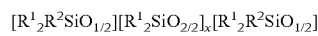

$[R^1_2R^2SiO_{1/2}][R^1_2SiO_{2/2}]_x[R^1_2R^2SiO_{1/2}]$ where $R^1$ is an alkyl group containing 1 to 30 carbon atoms, $R^2$ may be an $R^1$ alkyl group or a hydroxy group, the subscript "x" represents the degree of polymerization and is greater than 1000. Typically, the polydialkylsiloxane is a trimethylsiloxy terminated polydimethylsiloxane fluid having a degree of polymerization (x) that is sufficient to provide a polydimethylsiloxane fluid viscosity of at least 50,000 mm$^2$/s (or 50,000 centistokes, abbreviated as cS) at 23° C., alternatively (x) is sufficient to provide a polydimethylsiloxane fluid viscosity of at least 100,000 mm$^2$/s at 23° C. alternatively (x) is sufficient to provide a polydimethylsiloxane fluid viscosity of at least 500,000 mm$^2$/s at 23° C. Representative commercial products of trimethylsiloxy terminated polydimethylsiloxane fluids suitable as component A) include Dow Corning 200® fluids (Dow Corning Corporation, Midland Mich.) having a viscosity of at least 50,000 centistokes.

The polydialkylsiloxane may also be a mixture of various polydialkylsiloxanes. Furthermore, the polydialkylsiloxane may also be dissolved in a suitable solvent, such as a lower molecular weight (that is where x is less than 1000) polydialkylsiloxane.

B) The Aminofunctional Organopolysiloxane

Organopolysiloxanes are polymers containing siloxane units independently selected from $(R_3SiO_{1/2})$, $(R_2SiO_{2/2})$, $(RSiO_{3/2})$, or $(SiO_{4/2})$ siloxy units, where R may be any monovalent organic group. When R is a methyl group in the $(R_3SiO_{1/2})$, $(R_2SiO_{2/2})$, $(RSiO_{3/2})$, or $(SiO_{4/2})$ siloxy units of an organopolysiloxane, the siloxy units are commonly referred to as M, D, T, and Q units respectively. These siloxy units can be combined in various manners to form cyclic, linear, or branched structures. The chemical and physical properties of the resulting polymeric structures can vary. For example organopolysiloxanes can be volatile or low viscosity fluids, high viscosity fluids/gums, elastomers or rubbers, and resins depending on the number and type of siloxy units in the average polymeric formula. R may be any monovalent organic group, alternatively R is a hydrocarbon group containing 1 to 30 carbons, alternatively R is an alkyl group containing 1 to 30 carbon atoms, or alternatively R is methyl.

The aminofunctional organopolysiloxanes of the present invention are characterized by having at least one of the R groups in the formula $R_nSiO_{(4-n)/2}$ be an amino group. The amino functional group may be present on any siloxy unit having an R substituent, that is, they may be present on any $(R_3SiO_{1/2})$, $(R_2SiO_{2/2})$, or $(RSiO_{3/2})$ unit, and is designated in the formulas herein as $R^N$. The amino-functional organic group $R^N$ is illustrated by groups having the formula; $-R^3NHR^4$, $-R^3NR^4_2$, or $R^3NHR^3NHR^4$, wherein each $R^3$ is independently a divalent hydrocarbon group having at least 2 carbon atoms, and $R^4$ is hydrogen or an alkyl group. Each $R^3$ is typically an alkylene group having from 2 to 20 carbon atoms. $R^3$ is illustrated by groups such as; —CH$_2$CH$_2$—, —CH$_2$CH$_2$CH$_2$—, —CH$_2$CHCH$_3$—, —CH$_2$CH$_2$CH$_2$CH$_2$—, —CH$_2$CH(CH$_3$)CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH(CH$_2$CH$_3$)CH$_2$CH$_2$—, —CH$_2$CH$_2$CH$_2$CH$_2$CH$_2$CH$_2$CH$_2$CH$_2$—, and —CH$_2$CH$_2$CH$_2$CH$_2$CH$_2$CH$_2$CH$_2$CH$_2$CH$_2$CH$_2$—. The alkyl groups $R^4$ are as illustrated above for R. When $R^4$ is an alkyl group, it is typically methyl.

Some examples of suitable amino-functional hydrocarbon groups are; —CH$_2$CH$_2$NH$_2$, —CH$_2$CH$_2$CH$_2$NH$_2$, —CH$_2$CH(CH$_3$)NH$_2$, —CH$_2$CH$_2$CH$_2$CH$_2$NH$_2$, —CH$_2$CH$_2$CH$_2$CH$_2$CH$_2$NH$_2$, —CH$_2$CH$_2$CH$_2$CH$_2$CH$_2$CH$_2$NH$_2$, —CH$_2$CH$_2$NHCH$_3$, —CH$_2$CH$_2$CH$_2$NHCH$_3$, —CH$_2$CH(CH$_3$)CH$_2$NHCH$_3$, —CH$_2$CH$_2$CH$_2$CH$_2$NHCH$_3$, —CH$_2$CH$_2$NHCH$_2$CH$_2$NH$_2$, —CH$_2$CH$_2$CH$_2$NHCH$_2$CH$_2$NH$_2$, —CH$_2$CH$_2$CH$_2$NHCH$_2$CH$_2$CH$_2$NH$_2$, —CH$_2$CH$_2$CH$_2$CH$_2$NHCH$_2$CH$_2$CH$_2$NH$_2$, —CH$_2$CH$_2$NHCH$_2$CH$_2$NHCH$_3$, —CH$_2$CH$_2$CH$_2$NHCH$_2$CH$_2$CH$_2$NHCH$_3$, —CH$_2$CH$_2$CH$_2$CH$_2$NHCH$_2$CH$_2$CH$_2$CH$_2$NHCH$_3$, and —CH$_2$CH$_2$NHCH$_2$CH$_2$NHCH$_2$CH$_2$CH$_3$.

Alternatively, the amino functional group is —CH$_2$CH(CH$_3$)CH$_2$NHCH$_2$CH$_2$NH$_2$.

The aminofunctional organopolysiloxane used as component B) may be selected from those having the average formula;

$$[R_3SiO_{1/2}][R_2SiO_{2/2}]_a[RR^NSiO_{2/2}]_b[R_3SiO_{1/2}]$$

where;
a is 1-1000, alternatively 1 to 500, alternatively 1 to 200,
b is 1-100, alternatively 1 to 50, alternatively 1 to 10,
R is independently a monovalent organic group,
  alternatively R is a hydrocarbon containing 1-30 carbon atoms,
  alternatively R is a monovalent alkyl group containing 1-12 carbons, or alternatively R is a methyl group;
$R^N$ is as defined above.

The aminofunctional organopolysiloxane used as component B) may also be a combination of any of the aforementioned aminofunctional organopolysiloxanes. The aminofunctional organopolysiloxane may also be dissolved in a suitable solvent, such as a lower molecular weight organopolysiloxane or organic solvent.

Mixing in step (I) can be accomplished by any method known in the art to effect mixing of high viscosity materials. The mixing may occur either as a batch, semi-continuous, or continuous process. Mixing may occur, for example using, batch mixing equipment with medium/low shear include change-can mixers, double-planetary mixers, conical-screw mixers, ribbon blenders, double-arm or sigma-blade mixers; batch equipments with high-shear and high-speed dispersers include those made by Charles Ross & Sons (NY), Hockmeyer Equipment Corp. (NJ); batch mixing equipment such as those sold under the tradename Speedmixer®; batch equipment with high shear actions include Banbury-type (CW Brabender Instruments Inc., NJ) and Henschel type (Henschel mixers America, TX). Illustrative examples of continuous mixers/compounders include extruders single-screw, twin-screw, and multi-screw extruders, co-rotating extruders, such as those manufactured by Krupp Werner & Pfleiderer Corp (Ramsey, N.J.), and Leistritz (NJ); twin-screw counter-rotating extruders, two-stage extruders, twin-rotor continuous mixers, dynamic or static mixers or combinations of these equipments.

Step II) in the present process involves admixing;
C) 0.1 to 50 parts of a halide free quaternary ammonium surfactant containing at least 10 carbon atoms, and
a sufficient amount of water to form an emulsion.

C) The Quaternary Ammonium Surfactant

Component C) in the present process is a halide free quaternary ammonium surfactant containing at least 10 carbon atoms. As used herein "halide free" means the quaternary ammonium surfactant does not contain fluoride, chloride, bromide, or iodide as a counter-ion in the quaternary ammonium compound.

The halide free quaternary ammonium surfactant may have the formula;

$$R^5{}_aR^6{}_{(4-a)}N^+X^-,\text{ wherein}$$

the subscript "a" may vary from 1 to 4, alternatively "a" is 1.

$R^5$ is an organic group containing at least 10 carbon atoms,
$R^6$ is independently a hydrocarbon group containing 1 to 20 carbon atoms,
X is a halide free counter ion.

In the above formula $R^5$ is an organic group containing at least 10 carbon atoms. Representative, non-limiting examples of $R^5$ include alkyl groups such as decyl, undecyl, dodecyl, hexadecyl, octadecyl, and the like. $R^5$ may also be selected from those organic groups considered as being derived from "fatty acids or fatty alcohols" such as lauryl, cetyl, coco, stearyl, tallow, cocoyl, lauroyl, palmitoyl, myristoyl or stearoyl. Alternatively, $R^1$ is a coco group.

$R^6$ is independently a hydrocarbon group containing 1 to 20 carbon atoms. $R^6$ may be an alkyl group, alkenyl group, aryl, or alkylaryl group. Alternatively $R^6$ is an alkyl group containing 1 to 4 carbon atoms such as methyl, ethyl, propyl, or butyl. Alternatively $R^2$ is methyl or ethyl.

X is a halide free counter ion. Thus, X may be selected from methosulfate, etho-sulfate, acetate, tosylate, phosphate, or nitrate as possible counter ions.

Representative, non-limiting examples of commercially available quaternary ammonium salts suitable in the present process include;

| Generic name | Commercial name |
| --- | --- |
| coco trimethylammonium methosulfate | Luviquat Mono LS |
| coco trimethylammonium methosulfate | Surtec 932 |
| coco trimethylammonium methosulfate | Servamine KAC 458 |
| cetyl trimethylammonium methosulfate | Crodazosoft DBQ |
| stearyl trimethylammonium methosulfate | Empigen CM |
| cocoylcholine methosulfate | Surfactive VCC |
| lauroyl ethyltrimethylammonium methosulfate | Surfactive V 12 |
| myristoyl ethyltrimethylammonium methosulfate | Surfactive V 14 |
| palmitoyl ethyltrimethylammonium methosulfate | Surfactive V 16 |
| cetyl ethyldimethylammonium ethosulfate | Mecetronium Etilsulfate |
| coco ethyldimethylammonium ethosufalte | Dextrol AS-150 |
| cetyl trimethylammonium tosylate | Cetats |
| dimethyl PABAmidopropyl lauryldimethylammonium tosylate | Esccalol HP |
| bis-hydroxyethyl trimethylammonium nitrate | Ethoquad C/12 Nitrate |
| tallow trihydroxy ethylammonium acetate | Ethoquad T/13-50 |
| tallow trihydroxy ethylammonium acetate | Ethoquad T/13-27W |

An optional nonionic surfactant, designated herein as component D), may be also included in step II) of the present process. Some suitable nonionic surfactants which can be used include polyoxyethylene alkyl ethers, polyoxyethylene alkyl phenyl ethers, polyoxyethylene fatty acid esters, sorbitan fatty acid esters, and polyoxyethylene sorbitan fatty acid esters. Nonionic surfactants which are commercially available include compositions such as (i) 2,6,8-trimethyl-4-nonyl polyoxyethylene ether sold under the names Tergitol TMN-6 and Tergitol TMN-10; (ii) the C11-15 secondary alkyl polyoxyethylene ethers sold under the names Tergitol 15-S-7, Tergitol 15-S-9, Tergitol 15-S-15, Tergitol 15-S-30, and Tergitol 15-S-40, by the Dow Chemical Company, Midland, Mich.; octylphenyl polyoxyethylene (40) ether sold under the name Triton X405 by the Dow Chemical Company, Midland, Mich.; (iii) nonylphenyl polyoxyethylene (10) ether sold under the name Makon by the Stepan Company, Northfield, Ill.; (iv) ethoxylated alcohols sold under the name Trycol 5953 by Henkel Corp./Emery Group, Cincinnati, Ohio; and (v) ethoxylated alcohols sold under the name Brij by Uniqema (ICI Surfactants), Wilmington, Del., and ethoxylates of alkyl polyethylene glycol ethers based on the C10-Guerbet alcohol sold under the tradename Lutensol (BASF), such as Lutensol XP 79.

When the optional nonionic surfactant is used in step II), the amount may vary from 0.01 to 50 parts of the nonionic surfactant for every 100 parts of the polydialkylsiloxane used in the process.

Step II also involves the addition and mixing of water with the resulting mixture from step I), with component C) and optionally D). Typically 5 to 700 parts water are mixed for every 100 parts of the step I mixture to form an emulsion.

The mixing of the components in step II may be effected by the same mixing techniques as described above for step I). Mixing may also be effected using shear mixing techniques such as a rotor stator mixer, a homogenizer, a sonolator, a microfluidizer, a colloid mill, mixing vessels equipped with high speed spinning or with blades imparting high shear, or sonication to effect the formation of the emulsion.

In one embodiment the emulsion formed is a water continuous emulsion. Typically, the water continuous emulsion has dispersed particles of the step I) mixture, and having an average particle size less than 1000 μm. Alternatively, the average volume particle size of the emulsions prepared according to the inventive process is between 0.05 μm and 1000 μm; or between 0.1 μm and 500 μm; or between 0.1 μm and 100 μm; or between 1 and 10 μm.

The particle size of the present emulsions may be measured by laser diffraction. Suitable laser diffraction techniques are well known in the art. The particle size is obtained from a particle size distribution (PSD). The PSD can be determined on a volume, surface, and length basis. The volume particle size is equal to the diameter of the sphere that has the same volume as a given particle. The term Dv represents the average volume particle size of the polynuclear microcapsules. Dv 0.5 is the particle size measured in volume corresponding to 50% of the cumulative particle population. In other words if Dv 0.5=10 μm, 50% of the particle have an average volume particle size below 10 μm and 50% of the particle have a volume average particle size above 10 μm. Unless indicated otherwise all average volume particle sizes are calculated using Dv 0.5.

The amount of water added in step II) can vary from 5 to 700 parts per 100 parts by weight of the mixture from step I. The water is added to the mixture from step I at such a rate so as to form an emulsion of the mixture of step I. While this amount of water can vary depending on the selection of the amount of polydialkylsiloxane and aminofunctional organopolysiloxane present and the specific quaternary ammonium surfactant used, generally the amount of water is from 5 to 700 parts per 100 parts by weight of the step I mixture, alternatively from 5 to 100 parts per 100 parts by weight of the step I mixture, or alternatively from 5 to 70 parts per 100 parts by weight of the step I mixture.

The water added to the mixture from step I may be done in incremental portions, whereby each incremental portion comprises less than 30 weight % of the mixture from step I and each incremental portion of water is added successively to the previous after the dispersion of the previous incremental portion of water, wherein sufficient incremental portions of water are added to form an emulsion.

Additional additives and components may also be included in the emulsion compositions, such as preservatives, freeze/thaw additives, and various thickeners.

The present invention also relates to the emulsions produced by the present methods.

In one embodiment, the emulsions produced by the present process have an octamethylcyclotetrasiloxane and decamethylcyclopentasiloxane content that is less than 1 weigh percent of the total silicone emulsion. The cyclic siloxane content (that is octamethylcyclotetrasiloxanes ($D_4$) and decamethylcyclopentasiloxanes ($D_5$)) may be determined by harvesting the silicone phase of the emulsions with a mixture of polar and nonpolar organic solvents. The solvents containing any cyclic siloxanes can then be analyzed using common gas chromatography techniques.

The present emulsions may be formulated into personal care products. The personal care compositions may be in the form of a cream, a gel, a powder, a paste, or a freely pourable liquid. Generally, such compositions can generally be prepared at room temperature if no solid materials at room temperature are present in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care products may be functional with respect to the portion of the body to which they are applied, cosmetic, therapeutic, or some combination thereof. Conventional examples of such products include, but are not limited to: antiperspirants and deodorants, skin care creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, and powders, medicament creams, pastes or sprays including antiacne, dental hygienic, antibiotic, healing promotive, nutritive and the like, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier is readily apparent to one of ordinary skill in the art.

The compositions according to this invention can be used by the standard methods, such as applying them to the human body, e.g. skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the compositions according to the present invention may be used in a conventional manner for example for conditioning the skin. An effective amount of the composition for the purpose is applied to the skin. Such effective amounts generally range from about 1 mg/cm$^2$ to about 3 mg/cm$^2$. Application to the skin typically includes working the composition into the skin. This method for applying to the skin comprises the steps of contacting the skin with the composition in an effective amount and then rubbing the composition into the skin. These steps can be repeated as many times as desired to achieve the desired benefit.

The use of the compositions according to the invention on hair may use a conventional manner for conditioning hair. An effective amount of the composition for conditioning hair is applied to the hair. Such effective amounts generally range from about 0.5 g to about 50 g, preferably from about 1 g to about 20 g. Application to the hair typically includes working the composition through the hair such that most or all of the hair is contacted with the composition. This method for conditioning the hair comprises the steps of applying an effective amount of the hair care composition to the hair, and then working the composition through the hair. These steps can be repeated as many times as desired to achieve the desired conditioning benefit.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. All percentages are in wt. %. All measurements were conducted at 23° C. unless indicated otherwise.

Example 1

First, 283.5 grams of polydimethylsiloxane (Dow Corning® 200 Fluid) having a viscosity of 600,000 mm$^2$/s at 23° C. (cS) was added to a Max 500 dental mixer cup. Then, 31.6 grams of Dow Corning® 2-8566 Amino Fluid (an trimethylsiloxy terminated, dimethyl, methyl(aminoethylaminoisobutyl) polysiloxane, having a random distribution of two mole percent of silicon atoms substituted with methyl(aminoethylaminoisobutyl) functionality and of sufficient molecular weight to provide a rotational viscosity of 3,000 mPa·s (cP)) was added. The silicone fluids were blended using a DAC 600 FVZ SpeedMixer™ (FlackTek Inc.). Once homogenous, 4.5 grams of Lutensol® XP 79 (BASF), 7.4 grams of Luviquat® Mono LS (BASF), and 11.5 grams of deionized water were added. Mixing with the SpeedMixer™ yielded a white, opaque emulsion that was highly viscous. Subsequently, the emulsion was diluted with 110.2 grams of deionized water with mixing again from the SpeedMixer™. The particle size was measured using a Mastersizer 2000 (Malvern Instruments Ltd.). At the 50$^{th}$ percentile the particle size was 2.047 micrometers while the particle size at the 90$^{th}$ percentile was 3.782 micrometers.

After 14 days at 22° C., an aliquot of the emulsion from Example 1 was subjected to a mixture of polar and nonpolar organic solvents to harvest the internal phase of the emulsion. Using gas chromatography the solvents were analyzed for octamethylcyclotetrasiloxane (D4) and decamethylcyclopentasiloxane (D5) with values in the emulsion of 0.03 wt % and 0.05 wt %, respectively.

Following aging at 22° C. for 191 days, an aliquot of emulsion from Example 1 was subjected to a mixture of polar and nonpolar organic solvents to harvest the internal phase of the emulsion. Gas chromatography was used to determine the wt % of D4 and D5 which was found to be 0.23 wt % and 0.06 wt %, respectively.

A sample of emulsion from Example 1 was aged at 50° C. for 191 days and then subjected to a mixture of polar and nonpolar organic solvents to harvest the internal phase of the emulsion. With gas chromatography the wt % of D4 was found to be 0.40 wt %, while the wt % of D5 in the emulsion was found to be 0.07 wt %.

Example 2

63.0 grams of polydimethylsiloxane fluid (Dow Corning® 200 Fluid) having a viscosity of 600,000 mm$^2$/s at 23° C. (cS) and 7.0 grams of Dow Corning® 2-8566 Amino Fluid were added to a Max 100 dental mixer cup and mixed until homogenous with a DAC 150 FVZ SpeedMixer™ (Flacktek Inc). 1.0 grams of Lutensol® XP 79 (BASF), 1.7 grams SurTec® 932 (SurTec), and 2.5 grams of deionized water were added and the contents were mixed with the DAC 150 FVZ SpeedMixer™. Following this, the emulsion was diluted with 24.5 grams of deionized water followed by sufficient mixing to disperse the emulsion homogenously in the water. The median particle size of the emulsion was 2.756 micrometers and at the 90$^{th}$ percentile it was 4.70 micrometers.

Example 3

63.0 grams of polydimethylsiloxane fluid (Dow Corning® 200 Fluid) having a viscosity of 600,000 mm$^2$/s at 23° C. (cS) and 7.0 grams of Dow Corning® 2-8566 Amino Fluid were added to a Max 100 dental mixer cup and mixed until homogenous with a DAC 150 FVZ SpeedMixer™ (Flacktek, Inc). 1.0 grams of Lutensol® XP 79 (BASF), 1.2 grams Servamine KAC 458 (Elementis Specialties), and 3.0 grams of deionized water were added to the cup with mixing using the DAC 150 FVZ SpeedMixer™. Following this, the emulsion was diluted with 24.5 grams of deionized water with sufficient mixing. The median particle size of the emulsion was 2.756 micrometers and at the 90$^{th}$ percentile it was 4.70 micrometers.

Comparative Example 1

315.0 grams of polydimethylsiloxane fluid (Dow Corning® 200 Fluid) having a viscosity of 600,000 mm$^2$/s at 23° C. (cS) and 35.0 grams of Dow Corning® 2-8566 Amino Fluid were added to a Max 500 dental mixer cup and mixed until homogenous with a DAC 600 FVZ SpeedMixer™ (Flacktek, Inc). 5.0 grams of Lutensol® XP 79 (BASF), 8.5 grams of Arquad 16-29 (Akzo Nobel), and 12.50 grams deionized were added, followed by mixing until emulsion formation. Dilution was carried out with 122.50 grams of deionized water with sufficient mixing to thoroughly disperse the emulsion. Using a Mastersizer 2000, Malvern Instruments Ltd., the median particle size was determined as 2.12 micrometers with the 90$^{th}$ percentile particle size at 3.35 micrometers. Seven days after production, the internal phase of the emulsion was harvested with a mixture of polar and nonpolar organic solvents. The solvents were analyzed via gas chromatography. The wt % of D4 in the emulsion was found to be 0.14 wt %. D5 was contained in the emulsion at 0.11 wt %.

A sample of emulsion from comparative example 1 was aged at 22° C. for 200 days. Following aging, the emulsion sample was subjected to a mixture of polar and nonpolar organic solvents to harvest the internal phase. The solvents were analyzed with gas chromatography and the concentration of D4 and D5 in the emulsion was quantified at 0.67 wt % and 0.09 wt %, respectively.

From the emulsion prepared in comparative example 1, an aliquot was aged at 50° C. for 200 days. After aging, the emulsion sample was subjected to a mixture of polar and nonpolar organic solvents to harvest the internal phase. Following the harvest, the solvents were analyzed and the concentrations of D4 and D5 in the emulsion were quantified at 1.7 wt % and 0.23 wt %, respectively.

The invention claimed is:

1. A process for preparing an aminofunctional silicone emulsion comprising:
   I) forming a mixture of:
      A) 100 parts of a polydialkylsiloxane having a viscosity of at least 50,000 mm²/s at 23° C., and
      B) 0.1 to 100 parts of an aminofunctional organopolysiloxane,
   II) admixing:
      C) 0.1 to 50 parts of a halide free quaternary ammonium surfactant containing at least 10 carbon atoms, and
      a sufficient amount of water to form an emulsion,
   III) optionally, further shear mixing the emulsion,
   wherein the parts are per 100 parts of A), and wherein the emulsion has a particle size of between 1 and 10 μm and the emulsion has each of octamethylcyclotetrasiloxane ($D_4$) and decamethylcyclopentasiloxane ($D_5$) content less than 1 wt % of the emulsion.

2. The process of claim 1 wherein the polydialkylsiloxane is a trimethylsiloxy terminated polydimethylsiloxane having a viscosity of at least 100,000 mm²/s at 23° C.

3. The process of claim 1 wherein the aminofunctional organopolysiloxane has the average formula:

$$[R_3SiO_{1/2}][R_2SiO_{2/2}]_a[RR^NSiO_{2/2}]_b[R_3SiO_{1/2}]$$

where;
   a is 1-1000, b is 1-100,
   R is independently a monovalent organic group, and
   $R^N$ is an amino functional group.

4. The process of claim 3 wherein R is methyl and the amino functional group is $$-CH_2CH(CH_3)CH_2NHCH_2CH_2NH_2.$$

5. The process of claim 1 wherein the halide free quaternary ammonium surfactant has the formula:

$$R^5_aR^6_{(4-a)}N^+X^-, \text{ wherein}$$

a varies from 1 to 4,
$R^5$ is an organic group containing at least 10 carbon atoms,
$R^6$ is independently a hydrocarbon group containing 1 to 20 carbon atoms, and
X is a halide free counter ion.

6. The process of claim 5 where $R^5$ is lauryl, cetyl, coco, stearyl, tallow, cocoyl, lauroyl, palmitoyl, myristoyl or stearoyl.

7. The process of claim 6 where $R^6$ is methyl or ethyl.

8. The process of claim 6 where X is methosulfate, ethosulfate, acetate, tosylate, phosphate, or nitrate.

9. The process of claim 1 wherein step II) further comprises adding D) a nonionic surfactant.

10. The process of claim 9 wherein the nonionic surfactant is an alkyl polyethylene glycol ether based on C10-Guerbet alcohol.

11. An aminofunctional silicone emulsion produced by the method of claim 1, wherein the emulsion has a particle size of between 1 and 10 μm and the emulsion has each of octamethylcyclotetrasiloxane ($D_4$) and decamethylcyclopentasiloxane ($D_5$) content less than 1 wt % of the emulsion.

12. A personal care composition comprising the aminofunctional silicone emulsion of claim 11.

* * * * *